(12) United States Patent
Tu et al.

(10) Patent No.: US 7,645,897 B2
(45) Date of Patent: Jan. 12, 2010

(54) PROCESS FOR PRODUCING METAL OXIDE CATALYST

(76) Inventors: Xinlin Tu, c/o Toagosei Co., Ltd., 1-1, Funami-cho, Minato-ku, Nagoya-shi, Aichi (JP) 455-0027; Naomasa Furuta, c/o Toagosei Co., Ltd., 1-1, Funami-cho, Minato-ku, Nagoya-shi, Aichi (JP) 455-0027; Yuuichi Sumida, c/o Toagosei Co., Ltd., 1-1, Funami-cho, Minato-ku, Nagoya-shi, Aichi (JP) 455-0027

( * ) Notice: Subject to any disclaimer, the term of this patent is extended or adjusted under 35 U.S.C. 154(b) by 447 days.

(21) Appl. No.: 11/665,153

(22) PCT Filed: Jul. 13, 2005

(86) PCT No.: PCT/JP2005/012896

§ 371 (c)(1),
(2), (4) Date: Apr. 12, 2007

(87) PCT Pub. No.: WO2006/040863

PCT Pub. Date: Apr. 20, 2006

(65) Prior Publication Data

US 2009/0030224 A1    Jan. 29, 2009

(30) Foreign Application Priority Data

Oct. 15, 2004    (JP) .............................. 2004-301355
Apr. 14, 2005    (JP) .............................. 2005-116545

(51) Int. Cl.
*C07C 255/08*    (2006.01)
*B01J 21/06*    (2006.01)
*B01J 23/14*    (2006.01)
*B01J 23/22*    (2006.01)

(52) U.S. Cl. ....................... 558/319; 502/242; 502/248; 502/309; 502/312; 562/547; 562/549

(58) Field of Classification Search ........................ None
See application file for complete search history.

(56) References Cited

U.S. PATENT DOCUMENTS

| 5,994,580 | A | 11/1999 | Takahashi et al. |
| 2002/0115879 | A1 | 8/2002 | Hinago et al. |
| 2004/0030202 | A1 | 2/2004 | Chaturvedi et al. |

FOREIGN PATENT DOCUMENTS

| EP | 0761645 A2 | 3/1997 |
| JP | 07-010801 A | 1/1995 |
| JP | 09-316023 A | 12/1997 |
| JP | 10-028862 A | 2/1998 |
| JP | 10-036311 A | 2/1998 |
| JP | 10-137585 A | 5/1998 |
| JP | 2002-219362 A | 8/2002 |
| JP | 2004-025178 A | 1/2004 |
| WO | 2004/024665 A1 | 3/2004 |

OTHER PUBLICATIONS

Extended European Search Report dated Nov. 27, 2008.

*Primary Examiner*—Kamal A Saeed
(74) *Attorney, Agent, or Firm*—Sughrue Mion, PLLC

(57) ABSTRACT

A process for producing a high-performance catalyst for use in a reaction for acrylic acid production from propane or propylene through air oxidation, is provided. A process for producing a metal oxide catalyst having the following composition formula, the process comprising the following steps (1) and (2):

$MoV_iA_jB_kC_xO_y$    Composition formula (wherein A is Te or Sb; B is at least one element selected from the group consisting of Nb, Ta, and Ti; C is Si or Ge; i and j each are 0.01-1.5 and j/i is from 0.3 to 1.0; k is 0.001-3.0; x is 0.002-0.1; and y is a number determined by the oxidized states of the other elements), Step (1): a step in which an aqueous liquid containing Mo, V, metal A and metal B is evaporated to dryness and the solid matter obtained is calcined at a high temperature to thereby obtain a metal oxide; and Step (2): a step in which in an atmosphere containing substantially no water, a compound containing metallic element C is adhered to the metal oxide obtained in step (1) to form an oxide of metal C on the surface of the metal oxide.

4 Claims, No Drawings

PROCESS FOR PRODUCING METAL OXIDE CATALYST

TECHNICAL FIELD

The present invention relates to a process for producing a metal oxide catalyst for use in the production of acrylic acid by the vapor-phase contact oxidation of propane or propylene and in the production of acrylonitrile by the ammoxidation of propane.

BACKGROUND ART

In general, acrylic acid is produced by a two-stage oxidation reaction process which comprises a contact reaction of propylene and oxygen in the presence of a catalyst to produce acrolein, and then a contact reaction of the resultant acrolein and oxygen. Recently, however, processes for producing acrylic acid in one stage using propane as a starting material are being investigated, and many proposals have been made on catalysts for use therein. Representative examples thereof include metal oxide catalysts such as an [Mo, Te, V, Nb] system (patent document 1) and [Mo, Sb, V, Nb] systems (patent documents 2 and 3).

Furthermore, some patent applications were recently filed with respect to processes for producing a catalyst having improved performances as compared with those metal oxide catalysts. For examples, patent document 4 discloses a process for producing a catalyst which comprises reacting a molybdenum compound, a vanadium compound, and an antimony compound in an aqueous medium at 70° C. or higher, mixing the resultant aqueous reaction solution with a niobium compound, subsequently vaporizing the resultant mixture to dryness, and calcining the solid matter at a high temperature.

Patent document 5 discloses a method of catalyst modification which comprises impregnating an [Mo, Te, V] catalyst or an [Mo, Sb, V] catalyst with a solution containing one or more elements selected from the group consisting of W, Mo, Cr, Zr, Ti, Nb, Ta, V, B, Bi, Te, Pd, Co, Ni, Fe, P, Si, rare-earth elements, alkali metals, and alkaline earth metals to thereby deposit other metal(s) on the catalyst. The catalytic performances of the modified catalyst in the ammoxidation reaction of propane are evaluated therein.

Patent Document 1: JP-A-7-010801 (claims)
Patent Document 2: JP-A-9-316023 (claims)
Patent Document 3: JP-A-10-036311 (claims)
Patent Document 4: JP-A-10-137585 (claims)
Patent Document 5: JP-A-10-28862 (claims)

DISCLOSURE OF THE INVENTION

Problems that the Invention is to Solve

In order for the one-stage oxidation reaction of propane to attain a high selectivity to acrylic acid with any of the catalysts heretofore in use, it is necessary to heighten the proportion of water vapor to propane in the reaction gas. Specifically, water vapor proportions of 8.0 mol and higher per mol of propane have been used. However, there has been a problem that when conditions including such a high water vapor proportion are employed, the succeeding rectification step and wastewater treatment step require a considerable cost and the overall cost of acrylic acid production increases.

On the other hand, an industrial process for producing acrylic acid from propylene has already been established. However, the existing process is a two-stage process comprising a first-stage reaction for converting propylene to acrolein and a second-stage reaction for converting the acrolein to acrylic acid, and this process is complicated. There is room for improvement.

An object of the invention is to provide a process for producing a catalyst with which acrylic acid can be produced in high yield even under such reaction conditions that the proportion of water vapor is about 3.3 mol per mol of propane.

Another object is to provide a process for producing a catalyst with which acrylic acid can be produced from propylene in one stage.

Means for Solving the Problems

The present inventors made intensive investigations in order to overcome the problems described above. As a result, they have found that when a composite metal oxide obtained from an [Mo, Te, V] composite metal oxide or [Mo, Sb, V] composite metal oxide by adhering a specific metal compound thereto in the absence of water is used, then acrylic acid can be produced in high yield even under such reaction conditions that the proportion of water vapor to propane is relatively low. They have further found that with this composite metal oxide, acrylic acid can be produced in one stage from propylene as a raw material. The invention has been thus completed.

Namely, the invention provides a process for producing a metal oxide catalyst having the following composition formula, the process comprising the following steps (1) and (2):

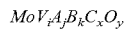   Composition formula (wherein A is Te or Sb; B is at least one element selected from the group consisting of Nb, Ta, and Ti; C is Si or Ge; i and j each are 0.01-1.5 and j/i is from 0.3 to 1.0; k is 0.001-3.0; x is 0.002-0.1; and y is a number determined by the oxidized states of the other elements)

Step (1): a step in which an aqueous liquid containing Mo, V, metal A, and metal B is evaporated to dryness and the solid matter obtained is calcined at a high temperature to thereby obtain a metal oxide; and Step (2): a step in which in an atmosphere containing substantially no water, a compound containing metallic element C is adhered to the metal oxide obtained in step (1) to form an oxide of metal C on the surface of the metal oxide.

The invention further provides a process for producing acrylic acid or acrylonitrile, which comprises subjecting propane or propylene to oxidation through a vapor-phase contact reaction or to ammoxidation in the presence of a metal oxide catalyst obtained by the process described above.

Advantages of the Invention

According to a production process of the invention, a metal oxide catalyst is easily obtained with which acrylic acid can be produced from propane or propylene in high yield. This metal oxide catalyst has such an excellent performance that even when low-water-vapor reaction conditions, which bring about a reduction in wastewater treatment and purification costs, are used, a selectivity to acrylic acid is not impaired. The catalyst attaining such a high selectivity is especially advantageous when a so-called recycling process is employed in which propane, in particular, is separated and recovered as a raw material.

According to another production process of the invention, acrylic acid can be produced from propylene in one stage.

Furthermore, this metal oxide catalyst can be used also for the ammoxidation of propane.

BEST MODE FOR CARRYING OUT THE INVENTION

The aqueous liquid containing Mo, V, metal A, and metal B, which is to be used in step (1) in the invention, preferably is an aqueous liquid obtained by the following method.

Namely, the preferred aqueous liquid containing Mo, V, metal A, and metal B is one prepared by first producing an aqueous liquid containing Mo, V, and metal A in the following manner and adding a metal B compound to the aqueous liquid obtained. The aqueous liquid containing Mo, V, and metal A may be obtained by mixing an Mo compound, V compound, and metal A compound, examples of which will be shown later, together in an aqueous medium and heating the resultant liquid mixture with stirring. The temperature at which the liquid mixture is heated is preferably 40° C. or higher, more preferably 40-100° C. The heating time is preferably 1-10 hours, more preferably 2-5 hours. Metal A is Te or Sb as stated above. Examples of the Te compound include metallic tellurium, tellurium dioxide, orthotelluric acid, metatelluric acid, and ammonium tellurate. The metallic tellurium preferably is one which has undergone wet pulverization beforehand or one in the form of fine particles of 5.0 μm or smaller obtained by reducing tellurium dioxide and telluric acid with a reducing agent in an aqueous medium. Preferred examples of the Sb compound are metallic antimony and antimony trioxide.

Examples of the Mo compound include ammonium molybdate, molybdenum oxide, and molybdic acid. Ammonium molybdate is preferred of these compounds because it is water-soluble. Preferred examples of the V compound include ammonium metavanadate and vanadium pentoxide.

The amounts of the Mo compound, metal A compound, and V compound to be added are as follows. The atomic proportions of the V and metal A (i and j) to the Mo are 0.01-1.5 each, and the atomic ratio of the metal A to the V (j/i) is 0.3-1.0. In case where the proportion of any of the Mo, V, and metal A is outside the range, the target metal oxide catalyst having high catalytic performances cannot be obtained.

By adding a metal B compound (metal B is at least one element selected from the group consisting of Nb, Ta, and Ti) to the reaction liquid obtained by the procedure described above, the aqueous liquid containing Mo, V, metal A, and metal B is obtained. From the standpoint of the performances of the metal oxide catalyst to be obtained, it is more preferred to add ammonia water when the metal B compound is added.

There are no particular limitations on the temperature of the liquid to which ammonia water and the metal B compound are to be added. Usually, the temperature thereof may be room temperature. By the addition of ammonia water and the metal B compound, a finely particulate precipitate is formed in the reaction liquid.

Examples of the metal B compound include oxides, nitrates, carboxylates, oxoacid salts, and oxalates. A metal B compound which is insoluble may be used in the form of a dispersion in water. In this case, however, the compound can be dissolved in the water by using oxalic acid or the like in combination therewith. The metal B compound is added in such an amount as to yield a metal oxide catalyst in which the atomic proportion of metal B is 0.001-3.0 when the Mo proportion is 1. In case where the proportion of metal B in the catalyst is lower than 0.001 when the Mo proportion is 1, the catalyst obtained is apt to deteriorate. On the other hand, in case where the proportion thereof exceeds 3.0, the catalyst obtained has reduced activity, resulting in a poor conversion of propane.

The amount of the ammonia water to be added is such that the molar proportion of the ammonia to the metal B is 0.4 or higher, preferably 0.8-3.0. In case where the ammonia amount is less than 0.4 in terms of molar proportion to the metal B, no effect is obtained. On the other hand, even when ammonia is used in an amount exceeding 3.0, the effect is not enhanced and a costly waste gas treatment is necessary.

It is preferred that nitric acid or ammonium nitrate be further added to the dispersion of a finely particulate precipitate obtained by adding ammonia water and a metal B compound. The amount of the nitric acid or ammonium nitrate to be added is such that the molar proportion of nitrate ions to the metal B is preferably 2.0-6.0, more preferably 2.2-4.0. In case where the amount of the nitrate ions added is outside the range, the effect of the addition is low.

The aqueous liquid obtained (usually in a slurry form) is heated and evaporated to dryness. The dried matter obtained is calcined in the presence of oxygen at a temperature of 250-380° C., preferably 280-360° C., for 0.5-10 hours, preferably 1-3 hours.

The solid obtained by the calcining is calcined in the absence of oxygen at a temperature of 480-640° C., preferably 570-620° C., for 0.1-5 hours, preferably 0.2-1.5 hours. Step (1) ends with this calcining.

A compound containing metallic element C (which is Si or Ge) (hereinafter this compound is referred to as metal C compound) is adhered to the metal oxide (hereinafter often referred to as catalyst precursor) obtained in step (1) described above, in an atmosphere in which water is absent. Examples of methods for adhesion include: a method in which the metal C compound is vaporized and this vapor is contacted with the metal oxide; and a method in which the metal oxide is immersed in an anhydrous organic-solvent solution of the metal C compound and the organic solvent is then volatilized. The catalyst precursor to be subjected to this adhesion of a metal C compound preferably is in the form of particles having a particle diameter of about from 0.1 mm to several millimeters. The catalyst precursor having such a particle size may be one obtained by sieving the metal oxide powder obtained in step (1) or may be one obtained by depositing the metal oxide powder on a support and then classifying it to obtain an even particle size.

As the metal C compound, use can be made of a metal C compound in the form of a chloride, organometallic compound, alkoxide, or the like. However, an alkoxide is preferred from the standpoint of handleability. Examples thereof include silicon tetrachloride, tetramethoxysilane, tetraethoxysilane, trimethoxysilane, triethoxysilane, trimethylsilane, triethylsilane, hexamethyldisilane, hexamethyldisilazane, hexamethylsiloxane, and tetraethoxygermanium. More preferred are tetraethoxysilane, triethoxysilane, triethylsilane, and tetraethoxygermanium.

The method in which the vapor of a metal C compound is adhered to particles of the catalyst precursor can be any of all known methods as long as the adhesion can be conducted in an atmosphere in which water is absent.

Simple methods usable on a laboratory scale include a method in which use is made of a scrubbing bottle (equipped with a filter) for use in removing dust particles or the like from a gas by passing the gas through a liquid placed in the cylindrical vessel. Namely, it is a method which comprises placing a liquid metal C compound in a cylindrical scrubbing bottle beforehand, passing a dehydrated inert gas (hereinafter often referred to as carrier gas) such as, e.g., dry nitrogen gas through the liquid to thereby produce a dehydrated inert-gas stream containing the vapor of the metal C compound in an amount corresponding to the vapor pressure, and bringing this stream into contact with particles of the catalyst precursor.

The vapor pressure of the metal C compound in the method described above depends on the temperature and pressure of the atmosphere. A simple method for increasing the vapor pressure is to elevate the temperature of the metal C compound placed in the cylindrical vessel. For selecting a temperature for this heating, it is advantageous to refer to the boiling point of the metal C compound. Examples of the boiling points of metal C compounds include 121.8° C. for tetramethoxysilane, 166.8° C. for tetraethoxysilane, 133.5° C. for triethoxysilane, 107° C. for triethylsilane, 253° C. for tetraethoxygermanium, and 57.6° C. for silicon tetrachloride.

Besides the temperature of the metal C compound, the flow rate of the carrier gas influences the amount of the metal C compound to be adhered to the catalyst precursor. A suitable carrier gas flow rate is 1,800-5,000 $hr^{-1}$ in terms of space velocity. It is preferred that a gas mixture having a metal C compound vapor concentration of 0.1-10,000 ppm, more preferably 1-1,000 ppm, be formed by using a suitable combination of a carrier gas flow rate and a vapor pressure of the metal C compound.

The carrier gas containing the metal C compound in that concentration is kept in contact with the catalyst precursor for an appropriate time period, whereby metal C can be adhered in that amount in the metal oxide catalyst which is determined by the composition formula given above, i.e., in an amount of 0.002-0.1 mol per mol of the Mo.

The adsorption of the metal C compound onto particles of the catalyst precursor is preferably conducted in the inside of a vessel blocked from the atmosphere, by fixed-layer adsorption or fluidizing-layer adsorption. The temperature of the catalyst precursor particles during the adsorption of the metal C compound is preferably from room temperature to 350° C., more preferably 50-300° C. When the vapor of the metal C compound comes into contact with the catalyst precursor kept at this temperature, the metal C compound adsorbed on the precursor surface rapidly changes into a metal oxide and is fixed to the precursor surface without fail.

In the case where fixed-layer adsorption is employed, use is made, for example, of a method comprising packing a cylindrical vessel with particles of the catalyst precursor, externally heating this vessel beforehand, and passing the carrier gas containing the vapor of the metal C compound through the vessel. Thus, an oxide of metal C can be formed on the precursor surface.

A metal oxide catalyst having the same performances can be produced also by the method which comprises impregnating the catalyst precursor with a solution containing a metal C compound to thereby adhere the metal C compound to the catalyst precursor and then converting the adherend metal C compound to an oxide.

In the case where the catalyst precursor to be subjected to the impregnation is temporarily exposed to the outside air, the catalyst precursor absorbs moisture in the outside air. It is therefore preferred that a dehydration treatment should be conducted before the impregnation treatment. The temperature for the dehydration is 50-300° C., preferably 70-250° C. In case where the dehydration temperature is below 50° C., no dehydration effect is obtained. In case where the dehydration temperature exceeds 300° C., the surface properties of the catalyst precursor change and a chemical reaction for depositing the metal C compound is difficult to proceed.

The organic solvent to be used is not particularly limited. However, it is preferred to use a hydrocarbon, e.g., toluene or hexane. The water content in the organic solvent is preferably 0.005% by mass or lower, more preferably 0.002% by mass or lower. In the case where the organic solvent has a water content exceeding 0.005% by mass, it is preferred to conduct dehydration by a known method, preferably the molecular sieve drying method.

The amount of the organic solvent to be used for the impregnation is 0.5-100 times, preferably 1-20 times, by volume the amount of the catalyst. In case where the amount of the organic solvent used is less than 0.5 times, the effect of modification is poor because the metal C compound cannot evenly adhere to the whole catalyst. On the other hand, even when the amount of the organic solvent used exceeds 100 times the amount of the catalyst, the effect is not enhanced and the solvent cost increases for the limited effect. The concentration of the metal C compound in the organic solvent is in the range of 0.5-300 µmol/mL, preferably 5-150 µmol/mL. In case where the concentration of the metal C compound in the organic solvent is lower than 0.5 µmol/mL, it is difficult to deposit metal C and the effect of deposition is low. On the other hand, in case where the concentration thereof exceeds 300 µmol/mL, deposition becomes uneven and the original modification effect is not exhibited.

After the catalyst precursor is impregnated with a solution containing a metal C compound and then taken out of the solution, the organic solvent is volatilized and removed from the precursor. The organic solvent may be directly volatilized. However, it is preferred that the catalyst precursor be washed with the dehydrated organic solvent to remove the raw-material C compound remaining unreacted before the organic solvent is volatilized. This method can further heighten the effect of modification.

For removing the organic solvent after the washing, a known method can be employed, such as distillation, centrifugal separation, or filtration. Thereafter, the catalyst precursor is heated to 50-300° C., whereby the metal C compound which has adhered to the catalyst precursor can be converted to a metal oxide and fixed to the precursor surface. The contents of the metal ingredients in the metal oxide catalyst of the invention obtained by fixing an oxide of metal C can be determined by fluorescent X-ray analysis.

The mechanism by which the adhesion of a metal C compound to the catalyst precursor improves selectivity has not been elucidated. However, it is presumed that sites which participate in side reactions were blocked by chemical reactions between the ligand of the metal C compound and surface functional groups of the catalyst precursor and the side reactions could hence be inhibited to thereby bring about the selectivity improvement. Incidentally, it is presumed that in case where a metal C compound is adhered in the presence of water, the metal C compound hydrolyzes and adheres not only to sites participating in side reactions but also to effective active sites to thereby considerably reduce activity.

It is preferred that the metal oxide catalyst obtained as particles be used in this particulate form. Pulverizing the particles may result in a decrease in catalytic performance. Although the metal oxide catalyst is usable in the support-free state, it may be used after having been deposited on a known support having an appropriate particle size, such as silica, alumina, silica-alumina, silicon carbide, or the like. There are no particular limitations on deposition amount, and a known deposition amount can be advantageously employed.

An explanation is given on the vapor-phase contact oxidation reaction of propane in which the metal oxide catalyst produced by the process described above is used. Propane and molecular oxygen (hereinafter referred to as oxygen gas) are introduced as raw materials for acrylic acid production into a reactor packed with the metal oxide catalyst and kept at a high temperature to thereby produce acrylic acid. Propane and oxygen gas may be separately introduced into the reactor and mixed with each other in the reactor. Alternatively, the two may be mixed beforehand and introduced in a mixed state into the reactor. For reaction control, it is preferred to use nitrogen, steam, carbon dioxide, or the like as a diluent gas in combination with the reactants.

In the case where propane and air are used as raw materials, the proportion of the air to the propane is preferably up to 30 times, more preferably 0.2-20 times, in terms of volume proportion. The proportion of the steam to the propane is preferably in the range of 0.8-8. In case where the proportion of the steam to the propane is lower than 0.8, a combustion reaction occurs consecutively, resulting in a low selectivity to acrylic acid. In case where the proportion thereof exceeds 8 times, the cost of a rectification step and wastewater treatment step increases, resulting in a disadvantage in profitability. The reaction temperature is in the range of 300-460° C., preferably in the range of 350-420° C. A suitable space velocity of the raw-material gas is 1,000-8,000 $hr^{-1}$. In case where the space velocity thereof is lower than 1,000 $hr^{-1}$, the space time yield of acrylic acid as the target compound decreases. In case where the space velocity thereof exceeds 8,000 $hr^{-1}$, the conversion decreases.

The propane remaining unreacted and the propylene as an intermediate product which are contained in the reaction gas discharged through the outlet of the reactor may be directly used as a fuel. However, the propane and propylene may be separated from other ingredients in the reaction gas, returned to the reactor, and reused. As a method for separating the unreacted propane gas from other ingredients including reaction products and the inert gas, use can be made of the known pressure-swing adsorption method (PSA method), organic-solvent adsorption method, or the like. The metal oxide catalyst produced by the invention is applicable also to the oxidation of propylene and the ammoxidation of propane, and acrylic acid or acrylonitrile can be synthesized in high yield. Conditions of the oxidation of propylene or ammoxidation of propane may be almost the same as the conditions of the vapor-phase contact oxidation of propane described above.

The invention will be explained below in more detail by reference to Examples and Comparative Examples. The metal oxide catalysts obtained in the Examples and Comparative Examples were evaluated for catalytic performances by the following method. Into a 10-mmΦ reaction tube made of quartz was packed 1.0 g (0.8-1.0 mL) of a catalyst having an average particle diameter of 0.5-1 mm. The reaction temperature in this reaction tube (the temperature measured with a thermocouple fixed to a central part of the catalyst layer) was set at 370° C. A mixed gas composed of 7.6% by volume propane, 14.2% by volume oxygen gas, 53.5% by volume nitrogen gas, and 24.7% by volume water vapor was fed to the reaction tube at a space velocity of 2,200 $/hr^{-1}$ to thereby produce acrylic acid.

The reaction products were analyzed for composition. Based on this, the conversion of the propane and the selectivity to acrylic acid which are represented by the following equations were calculated (each by mole).

Conversion of propane (%)=100×[(propane fed)−(unreacted propane)]/(propane fed)

Selectivity to acrylic acid (%)=100×(acrylic acid yielded)/ [(propane fed)−(unreacted propane)]

Yield of acrylic acid (%)=[(conversion of propane)×(selectivity to acrylic acid)]/100

In the case of propylene oxidation, the following were used.

Conversion of propylene (%)=100×[(propylene fed)−(unreacted propylene)]/(propylene fed)

Selectivity to acrylic acid (%)=100×(acrylic acid yielded)/ [(propylene fed)−(unreacted propylene)]

Selectivity to acrolein (%)=100×(acrolein yielded)/[(propylene fed)−(unreacted propylene)]

Yield of acrylic acid (%)=[(conversion of propane)×(selectivity to acrylic acid)]/100

EXAMPLE 1

Into a 500-mL flask made of glass were introduced 2.66 g of ammonium metavanadate, 15.45 g of ammonium molybdate, and 50 mL of distilled water. The solids were dissolved with stirring at a temperature around 80° C. After completion of the dissolution, the heating was stopped and 30 mL of an aqueous dispersion containing 1.46 g of tellurium metal particles (rod-shaped particles having an average major-axis length of 0.3 µm and an average minor-axis length of 0.1 µm) obtained by reducing tellurium dioxide with hydrazine was added to the solution. Furthermore, 1.0 g of 30% ammonia water was added dropwise thereto. The reaction liquid was stirred for several minutes, through which the temperature thereof became 50° C.

To this reaction liquid was added an aqueous solution obtained by dissolving 5.89 g of oxalic acid and 2.32 g of niobic acid in 160 mL of distilled water. The liquid mixture obtained was stirred for 5 minutes, and 4.0 g of ammonium nitrate was further added thereto. Thereafter, this mixture was evaporated to dryness with a 120° C. dryer.

The dried matter obtained was calcined at 320° C. for 1.5 hours in an air atmosphere. The solid particles thus obtained were calcined at 590° C. for 1.5 hours in a stainless-steel calcining tube to thereby obtain a metal oxide. Furthermore, particles having a particle diameter of 0.5-1 mm were taken out with sieves, and were used in the following experiment. As a result of fluorescent X-ray analysis for composition, the metal oxide (hereinafter referred to as four-metal oxide) was found to have the following atomic ratio: Mo/V/Te/Nb=1.0/ 0.28/0.14/0.16 (molar ratio).

The four-metal oxide obtained by the procedure described above was packed, in an amount of 1.0 g, into the space over a metal gauze placed in a silica tube. This tube was held at 200° C. for about 30 minutes while passing dry nitrogen gas therethrough at a flow rate of 0.2 L/min. Thereafter, the nitrogen gas line was connected to a scrubbing bottle containing tetraethoxysilane kept at 50° C. While the flow rate of nitrogen was kept at 0.5 L/min, the vapor of tetraethoxysilane was brought for 5 minutes into contact with the metal oxide particles kept at 200° C. Thus, a metal oxide catalyst was obtained.

This metal oxide catalyst was found to have the following composition: Mo/V/Te/Nb/Si=1.0/0.28/0.14/0.16/0.011 (molar ratio). The yield of acrylic acid, etc. in the oxidation reaction of propane using this catalyst are as shown in Table 1.

EXAMPLE 2

The same procedure as in Example 1 was conducted, except only that the vapor of triethoxysilane was brought into contact with the four-metal oxide produced as a catalyst precursor in Example 1. Thus, a metal oxide catalyst having a metal composition of Mo/V/Te/Nb/Si=1.0/0.28/0.14/0.16/0.012 (molar ratio) was obtained.

EXAMPLE 3

The same procedure as in Example 1 was conducted, except only that the vapor of triethylsilane was brought into contact with the four-metal oxide produced as a catalyst precursor in Example 1. Thus, a metal oxide catalyst having a metal composition of Mo/V/Te/Nb/Si=1.0/0.28/0.14/0.16/0.033 (molar ratio) was obtained.

EXAMPLE 4

The same procedure as in Example 1 was conducted, except only that the vapor of triethoxygermanium was brought into contact with the four-metal oxide produced as a catalyst precursor in Example 1. Thus, a metal oxide catalyst having a metal composition of Mo/V/Te/Nb/Ge=1.0/0.28/0.14/0.16/0.007 (molar ratio) was obtained.

The metal oxide catalysts obtained in Examples 2 to 4 were used to conduct a reaction for acrylic acid synthesis by propane oxidation. The results thereof are as shown in Table 1.

EXAMPLE 5

A 1.02-g portion of the four-metal oxide particles produced as a catalyst precursor in Example 1 was dehydrated by heating it at 220° C for 30 minutes in nitrogen and subsequently treated in the following manner without being exposed to the air. In a nitrogen atmosphere, the metal oxide particles which had been returned to room temperature were added to 7.5 mL of an n-hexane solution having a tetraethoxysilane concentration of 12 μmol/mL (the n-hexane used was one which had been dehydrated with molecular sieve 4A) and this mixture was sufficiently stirred. Thereafter, the mixture was heated at 80° C. for 30 minutes or longer in a nitrogen stream to vaporize the hexane.

The metal oxide catalyst obtained was used in the oxidation reaction of propane in the same manner as in the Examples given above. Before being used in the propane oxidation reaction, the metal oxide catalyst is heated to 370° C. in a column packed therewith to thereby convert the silicon atoms derived from tetraethoxysilane adhered by the procedure described above to an oxide. The metal oxide catalyst in this state had the following composition: Mo/V/Te/Nb/Si=1.0/0.28/0.14/0.16/0.016 (molar ratio).

EXAMPLE 6

A 1.02-g portion of the four-metal oxide particles produced as a catalyst precursor in Example 1 was dehydrated by heating it at 90° C. for 30 minutes in nitrogen and subsequently treated in the following manner without being exposed to the air.

In a nitrogen atmosphere, the metal oxide particles which had been returned to room temperature were added to 4.5 mL of a toluene solution having a tetraethoxysilane concentration of 100 μmol/mL (the toluene used was one which had been dehydrated with molecular sieve 4A) and this mixture was sufficiently stirred and then heated at 90° C. for 1 hour. In this heating, the solvent was refluxed. After completion of heating, the mixture was allowed to cool to room temperature and filtered in the air. The particles recovered were washed with 10 mL of a solvent, which was used in several portions. The metal oxide catalyst obtained was used in the oxidation reaction of propane in the same manner as in the Example 1.

Before being used in the propane oxidation reaction, the metal oxide catalyst is heated to 370° C. in a column packed therewith to thereby convert the silicon atoms derived from tetraethoxysilane adhered by the procedure described above to an oxide. The metal oxide catalyst in this state had the following composition: Mo/V/Te/Nb/Si=1.0/0.28/0.14/0.16/0.014 (molar ratio).

EXAMPLE 7

The same catalyst as in Example 6 was used in reaction evaluation, in which propylene was passed, in place of propane, through a reactor at the same flow rate to conduct an oxidation reaction. The reaction evaluation was conducted at 340° C. As a result, a conversion of the propylene of 98.4%, a selectivity to acrylic acid of 84.7%, and a selectivity to acrolein of 1.1% were obtained.

COMPARATIVE EXAMPLE 1

The four-metal oxide produced as a catalyst precursor in Example 1 was used as a catalyst to conduct a reaction for acrylic acid synthesis by propane oxidation in the same manner as in the Examples given above. The results thereof are as shown in Table 1.

COMPARATIVE EXAMPLE 2

The same procedure as in Comparative Example 1 was conducted, except only that the reaction temperature was changed to 360° C.

COMPARATIVE EXAMPLE 3

The same procedure as in Comparative Example 1 was conducted, except only that the reaction temperature was changed to 350° C. It can be seen from the results of a propane oxidation reaction using the catalysts of Comparative Example 2 and Comparative Example 3 that the regulation of reaction temperature, when employed as the only measure, is less effective in improving product selectivity in the oxidation reaction.

COMPARATIVE EXAMPLE 4

In a beaker was placed 0.094 g of a silica sol manufactured by Nissan Chemical Industries, Ltd. (trade name, Snowtex 30; aqueous dispersion of fine silica particles; $SiO_2$ concentration, 30 wt %). Thereto was added 5.0 g of distilled water to dissolve the sol. To this solution were added 2.5 g of the four-metal oxide particles produced as a catalyst precursor in Example 1. The resultant mixture was evenly mixed and then dried at 120° C. for 2 hours. The metal oxide catalyst obtained had the following metal composition: Mo/V/Te/Nb/Si=1.0/0.28/0.14/0.16/0.053 (molar ratio).

The catalyst obtained was used to conduct a reaction for acrylic acid synthesis by propane oxidation in the same manner as in the Examples and Comparative Examples given above.

COMPARATIVE EXAMPLE 5

The four-metal oxide produced as a catalyst precursor in Example 1 was used as a catalyst to conduct a reaction for acrylic acid synthesis by propylene oxidation in the same manner as in Example 7. A conversion of the propylene of 98.1%, a selectivity to acrylic acid of 73.4%, and a selectivity to acrolein of 3.4% were obtained at a reaction temperature of 340° C.

TABLE 1

| | C compound for vapor deposition | Molar ratio of deposit ingredients (M/Mo) | Results of reaction | | |
|---|---|---|---|---|---|
| | | | Conversion of P, % | Selectivity to AA, % | Yield of AA, % |
| Example 1 | tetraethoxysilane | Si/Mo = 0.011/1.0 | 60.3 | 75.4 | 45.4 |
| Example 2 | triethoxysilane | Si/Mo = 0.012/1.0 | 53.5 | 80.8 | 43.2 |
| Example 3 | triethylsilane | Si/Mo = 0.033/1.0 | 59.2 | 73.8 | 43.7 |
| Example 4 | tetraethoxygermanium | Ge/Mo = 0.045/1.0 | 57.8 | 74.6 | 43.1 |
| Example 5 | tetraethoxysilane | Si/Mo = 0.016/1.0 | 60.8 | 74.4 | 45.2 |
| Example 6 | tetraethoxysilane | Si/Mo = 0.014/1.0 | 56.4 | 81.2 | 45.8 |

| | C compound for impregnant liquid | Molar ratio of deposit ingredients (M/Mo) | Results of reaction | | |
|---|---|---|---|---|---|
| | | | Conversion of P, % | Selectivity to AA, % | Yield of AA, % |
| Comparative Example 1 | none | | 61.0 | 70.1 | 42.7 |
| Comparative Example 2 | none | | 54.3 | 71.2 | 35.8 |
| Comparative Example 3 | none | | 49.1 | 67.0 | 32.9 |
| Comparative Example 4 | silica sol (Snowtex 30) | Si/Mo = 0.053/1.0 | 59.0 | 69.6 | 41.1 |

P represents propane.
AA represents acrylic acid.
M is Si or Ge.

INDUSTRIAL APPLICABILITY

According to the metal oxide catalyst obtained by the invention, acrylic acid can be produced in high yield using propane and air or propylene and air as raw materials. Furthermore, acrylonitrile can be produced with the catalyst in high yield using propane and ammonia as raw materials.

The invention claimed is:

1. A process for producing a metal oxide catalyst having the following composition formula, the process comprising the following steps (1) and (2):

$$MoV_iA_jB_kC_xO_y \qquad \text{Composition formula}$$

(wherein A is Te or Sb; B is at least one element selected from the group consisting of Nb, Ta, and Ti; C is Si or Ge; i and j each are 0.01-1.5 and j/i is from 0.3 to 1.0; k is 0.001-3.0; x is 0.002-0.1; and y is a number determined by the oxidized states of the other elements), Step (1): a step in which an aqueous liquid containing Mo, V, metal A and metal B is evaporated to dryness and the solid matter obtained is calcined at a high temperature to thereby obtain a metal oxide; and Step (2): a step in which in an atmosphere containing substantially no water, a compound containing metallic element C is adhered to the metal oxide obtained in step (1) to form an oxide of metal C on the surface of the metal oxide.

2. The process for producing a metal oxide catalyst of claim 1, wherein in step (2), a vapor obtained by heating the compound containing metallic element C is adhered to the metal oxide obtained in step (1) to form an oxide of metal C on the surface of the metal oxide.

3. A process for producing acrylic acid, which comprises oxidizing propane or propylene through a vapor-phase contact reaction in the presence of a metal oxide catalyst produced by the process of claim 1 or 2.

4. A process for producing acrylonitrile, which comprises subjecting propane to ammoxidation in the presence of a metal oxide catalyst produced by the process of claim 1 or 2.

* * * * *